(12) United States Patent
Yous et al.

(10) Patent No.: US 7,462,741 B2
(45) Date of Patent: Dec. 9, 2008

(54) NAPHTHALENE COMPOUNDS

(75) Inventors: Said Yous, Loos (FR); Basile Peres, Foix (FR); Ahmed Sabaouni, Armentieres (FR); Pascal Berthelot, Haubourdin (FR); Michael Spedding, Le Vesinet (FR); Philippe Delagrange, Issy les Moulineaux (FR); Daniel-Henri Caignard, Boisemont (FR); Mark Millan, Le Pecq (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/823,771

(22) Filed: Jun. 28, 2007

(65) Prior Publication Data
US 2008/0004349 A1    Jan. 3, 2008

(30) Foreign Application Priority Data
Jun. 30, 2006    (FR)    .................................. 06 05917

(51) Int. Cl.
C07C 233/17    (2006.01)
A61K 31/165    (2006.01)
(52) U.S. Cl. ...................................... 564/219; 514/630
(58) Field of Classification Search ................ 564/219; 514/630
See application file for complete search history.

(56) References Cited
U.S. PATENT DOCUMENTS
5,616,614 A    4/1997    Yous et al.
6,583,319 B1    6/2003    Langlois et al.

FOREIGN PATENT DOCUMENTS
EP    0562956    9/1993
EP    0994102    4/2000

OTHER PUBLICATIONS

Marot C., et al., "Pharmacophoric search and 3D-QSAR comparative molecular field analysis studies on agonists of melationin sheep receptors" Journal of Medicinal Chemistry, vol. 41, No. 23, 1998, p. 4453-4465.
Preliminary Search Report for FR0605917 of Apr. 13, 2007.

*Primary Examiner*—Sikarl A Witherspoon
(74) *Attorney, Agent, or Firm*—Hueschen and Sage

(57) ABSTRACT

A compound selected from those of formula (I):

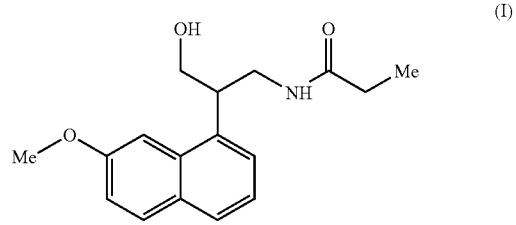

Medicinal products containing the same which are useful in the treatment of disorders of the melatoninergic system.

6 Claims, No Drawings

NAPHTHALENE COMPOUNDS

The present invention relates to new naphthalene compounds, to a process for their preparation and to pharmaceutical compositions containing them.

The compounds of the present invention are new and have very valuable pharmacological characteristics relating to melatoninergic receptors.

Numerous studies in the last ten years have demonstrated the key role of melatonin (N-acetyl-5-methoxytryptamine) in many physiopathological phenomena and in the control of circadian rhythms. Its half-life is quite short, however, owing to the fact that it is rapidly metabolized. Great interest therefore lies in the possibility of providing the clinician with melatonin analogues that are metabolically more stable, have an agonist or antagonist character and may be expected to have a therapeutic effect that is superior to that of the hormone itself.

In addition to their beneficial action on circadian rhythm disorders (J. Neurosurg. 1985, 63, pp. 321-341) and sleep disorders (Psychopharmacology, 1990, 100, pp. 222-226), ligands of the melatoninergic system have valuable pharmacological properties in respect of the central nervous system, especially anxiolytic and antipsychotic properties (Neuropharmacology of Pineal Secretions, 1990, 8 (3-4), pp. 264-272) and analgesic properties (Pharmacopsychiat., 1987, 20, pp. 222-223) as well as for the treatment of Parkinson's disease (J. Neurosurg. 1985, 63, pp. 321-341) and Alzheimer's disease (Brain Research, 1990, 528, pp. 170-174). Those compounds have also demonstrated activity in respect of certain cancers (Melatonin—Clinical Perspectives, Oxford University Press, 1988, pp. 164-165), ovulation (Science 1987, 227, pp. 714-720), diabetes (Clinical Endocrinology, 1986, 24, pp. 359-364), and in the treatment of obesity (International Journal of Eating Disorders, 1996, 20 (4), pp. 443-446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p. 50; WO 97.04094). For various species, including mammals, it has been possible for some of those receptors to be located and characterized. In order to be able to understand the physiological functions of those receptors better, it is of great advantage to have available selective ligands. Moreover, such compounds, by interacting selectively with one or other of those receptors, may be excellent medicaments for the clinician in the treatment of pathologies associated with the melatoninergic system, some of which have been mentioned above.

Besides the fact that they are new, the compounds of the present invention exhibit a very strong affinity for melatonin receptors.

They moreover have a strong affinity for the $5\text{-HT}_{2C}$ receptor, which has the effect of reinforcing the properties observed in the case of melatoninergic receptors, especially in the field of depression.

More specifically, the present invention relates to the compound of formula (I):

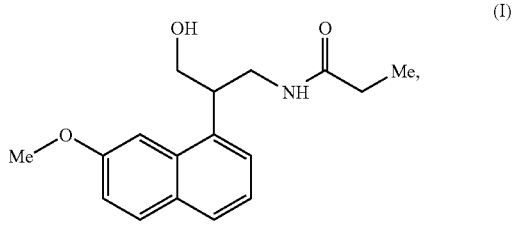

(I)

to enantiomers thereof, and to addition salts thereof with a pharmaceutically acceptable base.

Among the pharmaceutically acceptable bases there may be mentioned by way of non-limiting example sodium hydroxide, potassium hydroxide, triethylamine, tert-butylamine etc.

The invention even more specifically relates to the compounds which are N-[3-hydroxy-2-(7-methoxy-1-naphthyl)propyl]propanamide, N-[(2S)-3-hydroxy-2-(7-methoxy-1-naphthyl)propyl]propanamide and N-[(2R)-3-hydroxy-2-(7-methoxy-1-naphthyl)propyl]-propanamide.

The addition salts of preferred compounds of the invention with a pharmaceutically acceptable base form an integral part of the invention.

The invention relates also to a process for the preparation of compound of formula (I), which process is characterized in that there is used as starting material the compound of formula (II):

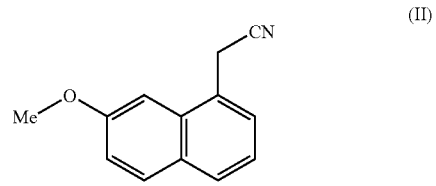

(II)

which is subjected to the action of dimethyl carbonate in a basic medium to yield the compound of formula (III):

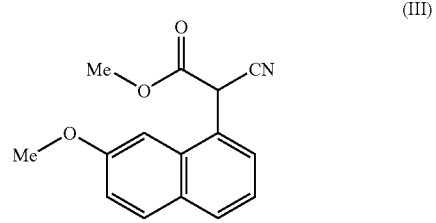

(III)

which is subjected to reduction in the presence of a hydride to yield the compound of formula (IV):

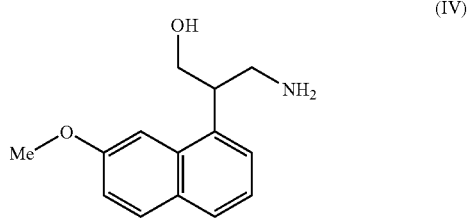

(IV)

with which propanol chloride is condensed to yield the compound of formula (I), which may be purified according to a conventional separation technique, which is converted, if desired, into its addition salts with a pharmaceutically acceptable base and the enantiomers of which may be separated on a chiral column according to a conventional separation technique.

Pharmacological study of the compounds of the invention has shown them to be atoxic, to have strong selective affinity for melatonin receptors and to have significant activities in respect of the central nervous system; and, in particular, therapeutic properties in respect of sleep disorders, antidepressive, anxiolytic, antipsychotic and analgesic properties and properties in respect of microcirculation have been found, enabling it to be established that the compounds of the invention are useful in the treatment of stress, sleep disorders, anxiety, seasonal affective disorder or major depression, cardiovascular pathologies, pathologies of the digestive system, insomnia and fatigue due to jet lag, schizophrenia, panic attacks, melancholia, appetite disorders, obesity, insomnia, psychotic disorders, epilepsy, diabetes, Parkinson's disease, senile dementia, various disorders associated with normal or pathological aging, migraine, memory loss and Alzheimer's disease, and in cerebral circulation disorders. In another field of activity, it appears that, in treatment, the compounds of the invention can be used in sexual dysfunctions, that they have ovulation-inhibiting and immunomodulating properties and that they may potentially be used in the treatment of cancers.

The compounds will preferably be used in the treatment of major depression, seasonal affective disorder, sleep disorders, cardiovascular pathologies, pathologies of the digestive system, insomnia and fatigue due to jet lag, appetite disorders and obesity.

For example, the compounds will be used in the treatment of major depression, seasonal affective disorder and sleep disorders.

The present invention relates also to pharmaceutical compositions comprising at least one compound of formula (I) on its own or in combination with one or more pharmaceutically acceptable excipients.

Among the pharmaceutical compositions according to the invention there may be mentioned more especially those that are suitable for oral, parenteral, nasal, per- or transcutaneous, rectal, perlingual, ocular or respiratory administration and especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the route of administration, the nature of the therapeutic indication or any associated treatments and ranges from 0.01 mg to 1 g per 24 hours in one or more administrations.

The following Examples illustrate the invention but do not limit it in any way.

EXAMPLE 1

N-[3-Hydroxy-2-(7-methoxy-1-naphthyl)propyl]propanamide

Step A: Methyl cyano(7-methoxy-1-naphthyl)acetate (7-Methoxy-naphth-1-yl)acetonitrile (20 g) is dissolved in 150 ml of anhydrous tetrahydrofuran. Sodium hydride (202.8 mmol) is added at ambient temperature, and the mixture is refluxed for 30 minutes. Dimethyl carbonate (12 ml) is added with caution, and the reaction mixture is refluxed for 30 minutes. The mixture is poured into ice-cold water, and the aqueous phase is acidified with 21 ml of 37% hydrochloric acid solution and then extracted twice with 100 ml of ether. The organic phase is washed with water, dried, decolored and evaporated. The oil obtained is precipitated from ether, and the precipitate formed is filtered off under suction and then recrystallized to yield the title product in the form of a white solid.

Melting point: 80-82° C.

Step B:
3-Amino-2-(7-methoxy-1-naphthyl)-1-propanol hydrochloride

Aluminium chloride (80 mmol), dissolved in 200 ml of anhydrous ether, is added to a suspension of lithium aluminium hydride at 0° C. in 300 ml of anhydrous ether. After stirring for 10 minutes, the compound obtained in Step A (20 mmol), dissolved in 200 ml of anhydrous ether, is added. After 30 minutes, the mixture is hydrolyzed, with caution and in the cold state, using sodium hydroxide solution (10 g; 40 ml). The precipitate formed is then filtered off and washed with copious amounts of ether. The residue obtained after evaporation is taken up in water and the aqueous phase is extracted with dichloromethane. The organic phase is then washed with water, dried and decolored, and is then treated with gaseous hydrogen chloride and evaporated. The oil obtained is precipitated from ethyl acetate, and the precipitate formed is filtered off under suction and then recrystallized to yield the title product in the form of a white solid.

Melting point: 164-166° C.

Step C: N-[3-Hydroxy-2-(7-methoxy-1-naphthyl)propyl]propanamide

The compound obtained in Step B (3.73 mmol) is dissolved in 100 ml of a mixture of water and ethyl acetate (50/50). Potassium carbonate (11.2 mmol) is added and the reaction mixture is cooled to 0° C. Using an ice bath. Propanol chloride (4.6 mmol) is added dropwise and the mixture is stirred for 15 minutes in the cold state. When the reaction is complete, the organic phase is washed with hydrochloric acid solution (1M), washed with water, dried and evaporated under reduced pressure. The solution obtained is recrystallized from acetonitrile to yield the title product in the form of a white solid.

Melting point: 128-129° C.

Elemental microanalysis:

| % | C | H | N |
|---|---|---|---|
| Calculated: | 71.05 | 7.36 | 4.77 |
| Found: | 70.82 | 7.39 | 4.70 |

The compound obtained in Example 1 is purified on a chiral column (R,R) WHELK 0-1 with eluant toluene/n-propanol (100/25) and a detection at 340 nm, to yield Examples 2 and 3:

EXAMPLE 2

N-[(2S)-3-Hydroxy-2-(7-methoxy-1-naphthyl)propyl]propanamide

EXAMPLE 3

N-[(2R)-3-Hydroxy-2-(7-methoxy-1-naphthyl)propyl]propanamide

PHARMACOLOGICAL STUDY

EXAMPLE A

Acute Toxicity Study

The acute toxicity was evaluated after oral administration to groups each comprising 8 mice (26±2 g). The animals were observed at regular intervals during the course of the first day,

EXAMPLE B

Forced Swimming Test

The compounds of the invention are tested in a behavioral model, the forced swimming test.

The apparatus is composed of a plexiglass cylinder filled with water. The animals are tested individually for a session of 6 minutes. At the start of each test, the animal is placed in the center of the cylinder. The time spent immobile is recorded. The animal is considered to be immobile when it stops struggling and remains immobile on the surface of the water, making only those movements which allow it to keep its head above water.

Following administration 40 minutes before the start of the test, the compounds of the invention significantly reduce the time spent immobile, which indicates their antidepressive activity.

EXAMPLE C

Melatonin $MT_1$ and $MT_2$ Receptor Binding Study

The $MT_1$ or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities of the compounds tested ($K_i$) to be determined.

By way of example, the compound obtained in Example 1 has a $K_i(MT_1)$ of 1.4 nM and a $K_i(MT_2)$ of 3.2 nM.

EXAMPLE D

Serotoninergic 5-$HT_{2C}$ Receptor Binding Study

The affinity of the compounds for the human 5-$HT_{2C}$ receptor is evaluated on membrane preparations from CHO cells stably expressing that receptor.

Incubation is carried out in 50 mM TRIS buffer, pH 7.4 containing 10 mM $MgCl_2$ and 0.1% BSA, in the presence of [$^3$H]-mesulergine (1 nM) and 25 fmol/ml of receptor. Non-specific binding is determined in the presence of 10 μM mianserin.

The reaction is stopped by the addition of 50 mM TRIS buffer, pH 7.4 followed by a filtration step and 3 successive rinses: the radioactivity bound to the membranes remaining on the filters (GF/B pretreated with 0.1% PEI) is determined by liquid scintillation counting.

The results obtained show that the compounds of the invention have affinity for the 5-$HT_{2C}$ receptor, with $K_i$ values<10 μM.

EXAMPLE E

Action of Compounds of the Invention on the Circadian Rhythms of Locomotive Activity of the Rat The involvement of melatonin in influencing, by day/night alternation, the majority of physiological, biochemical and behavioral circadian rhythms has made it possible to establish a pharmacological model for use in the search for melatoninergic ligands.

The effects of the compounds are tested on numerous parameters and, in particular, on the circadian rhythms of locomotive activity, which constitute a reliable indicator of the activity of the endogenous circadian clock.

In this study, the effects of such compounds on a particular experimental model, namely the rat placed in temporal isolation (permanent darkness), is evaluated.

Experimental Protocol

One-month-old male rats are subjected, as soon as they arrive at the laboratory, to a light cycle of 12 hours' light per 24 hours (LD 12:12).

After 2 to 3 weeks' adaptation, they are placed in cages fitted with a wheel connected to a recording system, in order to detect the phases of locomotive activity and thus monitor the nychthemeral rhythms (LD) or circadian rhythms (DD).

As soon as the rhythms recorded show a stable pattern during the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualization of the rhythms of activity:

influence on the rhythms of activity by the light/dark cycle, disappearance of the influence on the rhythms in permanent darkness, influence on the activity by the daily administration of the compound; transitory or durable effect.

A software package makes it possible:

to measure the duration and intensity of the activity, the period of the rhythm of the animals during free course and during treatment, possibly to demonstrate by spectral analysis the existence of circadian and non-circadian (for example ultradian) components.

Results

The compounds of the invention clearly appear to allow powerful action on the circadian rhythm via the melatoninergic system.

EXAMPLE F

Light/Dark Cages Test

The compounds of the invention are tested in a behavioral model, the light/dark cages test, which allows the anxiolytic activity of the compounds to be demonstrated.

The apparatus consists of two polyvinyl boxes covered with plexiglass. One of the boxes is in darkness. A lamp is placed above the other box, yielding a light intensity of approximately 4000 lux in the center of the box. An opaque plastic tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

Following administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE G

Pharmaceutical Composition: Tablets

| | |
|---|---|
| 1000 tablets each containing 5 mg of N-[3-hydroxy-2-(7-methoxy-1-naphthyl)-propyl]propanamide (Example 1) | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A compound selected from N-[3-hydroxy-2-(7-methoxy-1-naphthyl)propyl]propanamide of formula (I):

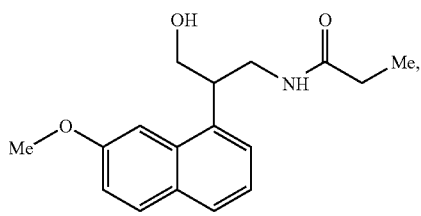

its enantiomers, and addition salts thereof with a pharmaceutically acceptable base.

2. The compound of claim 1, which is selected from N-[(2S)-3-hydroxy-2-(7-methoxy-1-naphthyl)propyl]propanamide, and addition salts thereof with a pharmaceutically acceptable base.

3. The compound of claim 1, which is selected from N-[(2R)-3-hydroxy-2-(7-methoxy-1-naphthyl)propyl]propanamide, and addition salts thereof with a pharmaceutically acceptable base.

4. A pharmaceutical composition comprising a compound of claim 1 or an addition salt thereof with a pharmaceutically acceptable base alone or in combination with one or more pharmaceutically acceptable excipients.

5. A method for treating a living animal body, including a human, afflicted with a disorder of the melatoninergic system comprising the step of administering to the living animal body, including a human, an amount of the compound of claim 1 which is effective for treatment of the disorder.

6. The method of claim 5, wherein the disorder is selected form sleep disorders, stress, anxiety, major depression or seasonal affective disorder, cardiovascular pathologies, pathologies of the digestive system, insomnia and fatigue due to jet lag, schizophrenia, panic attacks, melancholia, appetite disorders, obesity, insomnia, psychotic disorders, epilepsy, diabetes, Parkinson's disease, senile dementia, migraine, memory loss, Alzheimer's disease, and cerebral circulation disorders.

* * * * *